(12) United States Patent
Furnish et al.

(10) Patent No.: US 11,654,262 B2
(45) Date of Patent: May 23, 2023

(54) HANDLE ASSEMBLY FOR CONTROLLING A STEERABLE CATHETER

(71) Applicant: FREUDENBERG MEDICAL, LLC, Carpinteria, CA (US)

(72) Inventors: Greg Furnish, Louisville, KY (US); Cody Wetzel, New Salisbury, IN (US); Timothy S. Zeis, Charlestown, IN (US)

(73) Assignee: FREUDENBERG MEDICAL, LLC, Carpinteria, CA (US)

( * ) Notice: Subject to any disclaimer, the term of this patent is extended or adjusted under 35 U.S.C. 154(b) by 344 days.

(21) Appl. No.: 17/002,830

(22) Filed: Aug. 26, 2020

(65) Prior Publication Data

US 2022/0062587 A1    Mar. 3, 2022

(51) Int. Cl.
*A61M 25/01*    (2006.01)

(52) U.S. Cl.
CPC .... *A61M 25/0136* (2013.01); *A61M 25/0147* (2013.01)

(58) Field of Classification Search
CPC .......... A61M 25/0136; A61M 25/0147; A61M 25/01; A61M 25/0105; A61M 25/0133; A61M 2025/015; A61M 2025/0177; A61B 1/0052; A61B 1/00; A61B 1/005; A61B 1/0051; A61B 1/0057
See application file for complete search history.

(56) References Cited

U.S. PATENT DOCUMENTS

| | | |
|---|---|---|
| 5,462,527 A | 10/1995 | Stevens-Wright et al. |
| 5,531,686 A | 7/1996 | Lundquist et al. |
| 5,891,088 A | 4/1999 | Thompson et al. |
| 6,829,497 B2 | 12/2004 | Mogul |
| 7,269,453 B2 | 9/2007 | Mogul |
| 8,043,288 B2 * | 10/2011 | Dando ............... A61B 18/1492 606/41 |
| 8,583,260 B2 | 11/2013 | Knudson |
| 8,777,929 B2 | 7/2014 | Schneider et al. |
| 8,808,345 B2 | 8/2014 | Clark et al. |
| 8,958,861 B2 | 2/2015 | Plascencia, Jr. et al. |
| 8,979,740 B2 | 3/2015 | Butler |
| 9,694,159 B2 | 7/2017 | Schneider et al. |

(Continued)

FOREIGN PATENT DOCUMENTS

| | | |
|---|---|---|
| EP | 3662960 A1 | 6/2020 |
| WO | 2019157303 A1 | 8/2019 |
| WO | 2020123774 A1 | 6/2020 |

*Primary Examiner* — Jason E Flick
(74) *Attorney, Agent, or Firm* — Dickinson Wright PLLC

(57) ABSTRACT

A handle assembly for controlling a steerable catheter includes a handle extending about a longitudinal axis from a proximal end to a distal end. A lumen extends through the handle to a distal tip extending outwardly from the distal end of the handle and a pair of control wires are interconnected to the distal end of extend the lumen. A lever assembly is disposed within the handle and includes a lever rotatable about a lever axis to control deflection of the distal end of the lumen. The lever assembly includes a first and second gear assembly disposed in opposing relationship to one another and offset relative to the longitudinal axis for allowing the lumen to pass therebetween. Each of the gear assemblies are interconnected to one of the pair of control wires to individually pull a respective one of the control wires in response to rotation of the lever.

17 Claims, 10 Drawing Sheets

(56) References Cited

U.S. PATENT DOCUMENTS

| | | |
|---|---|---|
| 10,022,521 B2 | 7/2018 | Knudson |
| 2011/0270172 A1* | 11/2011 | Selkee .............. A61M 25/0136 |
| | | 604/95.04 |
| 2012/0226228 A1 | 9/2012 | Butler |
| 2018/0071487 A1 | 3/2018 | Khuu et al. |
| 2019/0029498 A1* | 1/2019 | Mankowski ......... A61B 1/0052 |
| 2020/0222667 A1 | 7/2020 | Tang et al. |

* cited by examiner

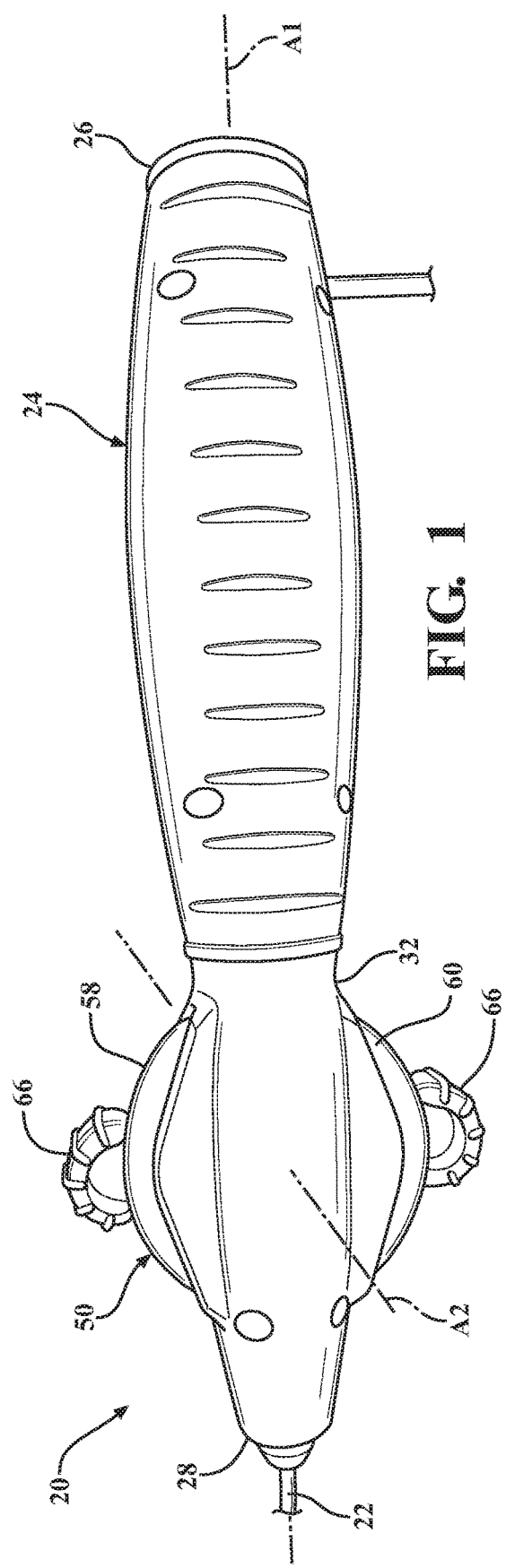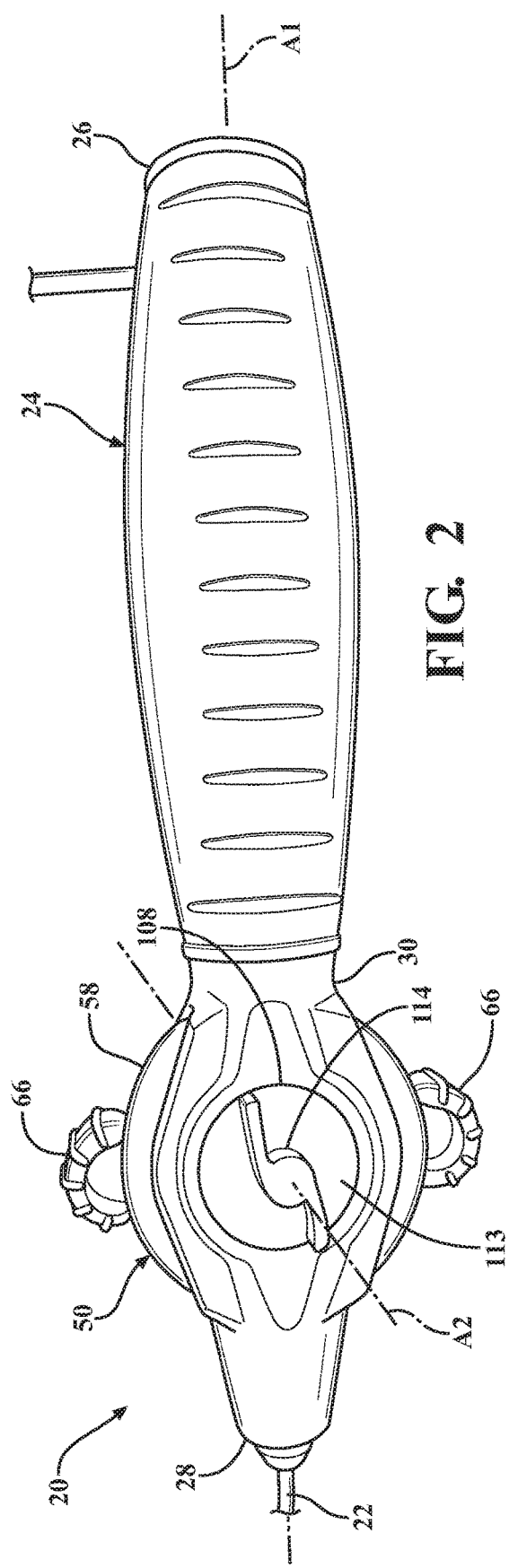

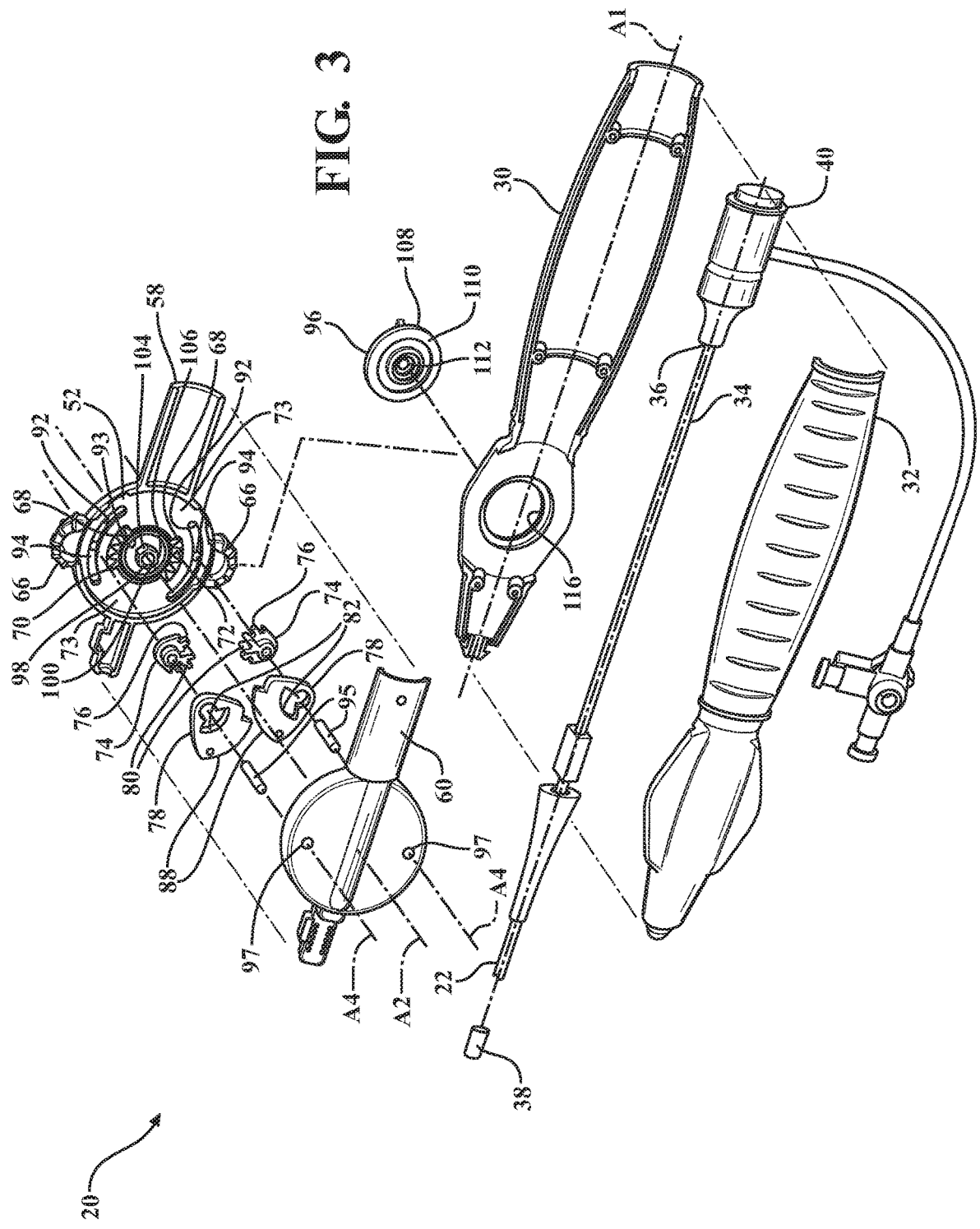

HANDLE ASSEMBLY FOR CONTROLLING A STEERABLE CATHETER

BACKGROUND OF THE INVENTION

1. Field of the Invention

The subject disclosure relates in general to steerable catheters and more particularly to a lever-style handle assembly for supporting and controlling a steerable catheter.

2. Description of the Related Art

This section provides background information related to the present disclosure which is not necessarily prior art.

Catheters are commonly used for non-invasive medical procedures and include a distal tip that is placed within a body vessel of a patient and deflectable in response to a controlling movement of an associated control handle. In a lever-style control handle, the distal tip of the catheter is selectively deflected into a curved configuration using a lever on the control handle. The lever is often operably connected to a pair of control wires that are pushed and pulled responsive to actuation of the lever in order to cause the distal tip of the catheter to deflect. However, the prior art lever-style control handles often require the wrapping of the control wires around a pair of pulleys to effectuate deflection of the distal tip, such as shown US 2012/0226228. Accordingly, the prior art lever-style control handles have a number of drawbacks.

Initially, the lever-style control handle disclosed in US 2012/0226228 requires that both wires are connected directly to the lever to effectuate deflection of the catheter, which causes a compressing force to be applied to one of the control wires or requires the use of a highly elastic wire during rotation of the lever. However, the control wires are not as strong when under compression as when under tension, and thus the pushing action results in bending of the control wires, leading to loss of their structural integrity, even to the point of breaking. Such a concern requires designs with material changes, leading to increased costs for the control handles. Further, as noted above, the prior art designs wrap the control wires around respective pulleys to effectuate deflection, which results in a low bending radius relative to a width of the control handle, requiring the control wires to undergo strain during wrapping around the pulleys. As a result, this low bending radius limits material choices, and thus again may require designs with material changes to the control wires to prevent their degradation.

Accordingly, there remains a continuing need for a lever-style control handle which reduces stress on the control wires to effectuate deflection of the distal tip of the catheter.

SUMMARY OF THE INVENTION

This section provides a general summary of the invention and is not intended to be a comprehensive disclosure of its full scope, aspects, objectives, and/or all of its features.

A handle assembly for supporting and controlling a steerable catheter includes a handle extending about a longitudinal axis from a proximal end to a distal end. A lumen extends through the handle along the longitudinal axis to a distal tip extending outwardly from and terminating in spaced relationship with the distal end of the handle. A pair of control wires are interconnected to the distal tip and extend through the lumen from the distal tip to within the handle. A lever assembly is disposed at least partially within the handle and includes a lever rotatable about a lever axis to control deflection of the distal tip of the lumen. The lever assembly includes a first gear assembly and a second gear assembly each disposed in opposing relationship to one another and offset relative to the longitudinal axis for allowing the lumen to pass therebetween. Each of the first and second gear assemblies are interconnected to a respective one of the pair of control wires for individually pulling the control wires in response to rotation of the lever.

As will be described in more detail below, the subject handle assembly provides for a lever-style control handle that, through the positioning of the gear assemblies offset from the longitudinal axis and configured to individually pull the control wires in response to rotation of the lever, results in reduced levels of non-tension force to the control wires while still allowing the lumen to pass through and be aligned along a center of the handle.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 1 is a first side view of a handle assembly illustrating a handle extending about a longitudinal axis from a proximal end to a distal end and including a lever assembly having a lever rotatable about a lever axis for controlling a steerable catheter;

FIG. 2 is a second side view of the handle assembly illustrating a tensioning mechanism of the lever assembly for allowing a user to adjust a resistance to rotation of the lever;

FIG. 3 is an exploded perspective view of the handle assembly;

DETAILED DESCRIPTION OF THE ENABLING EMBODIMENTS

Figure 4:
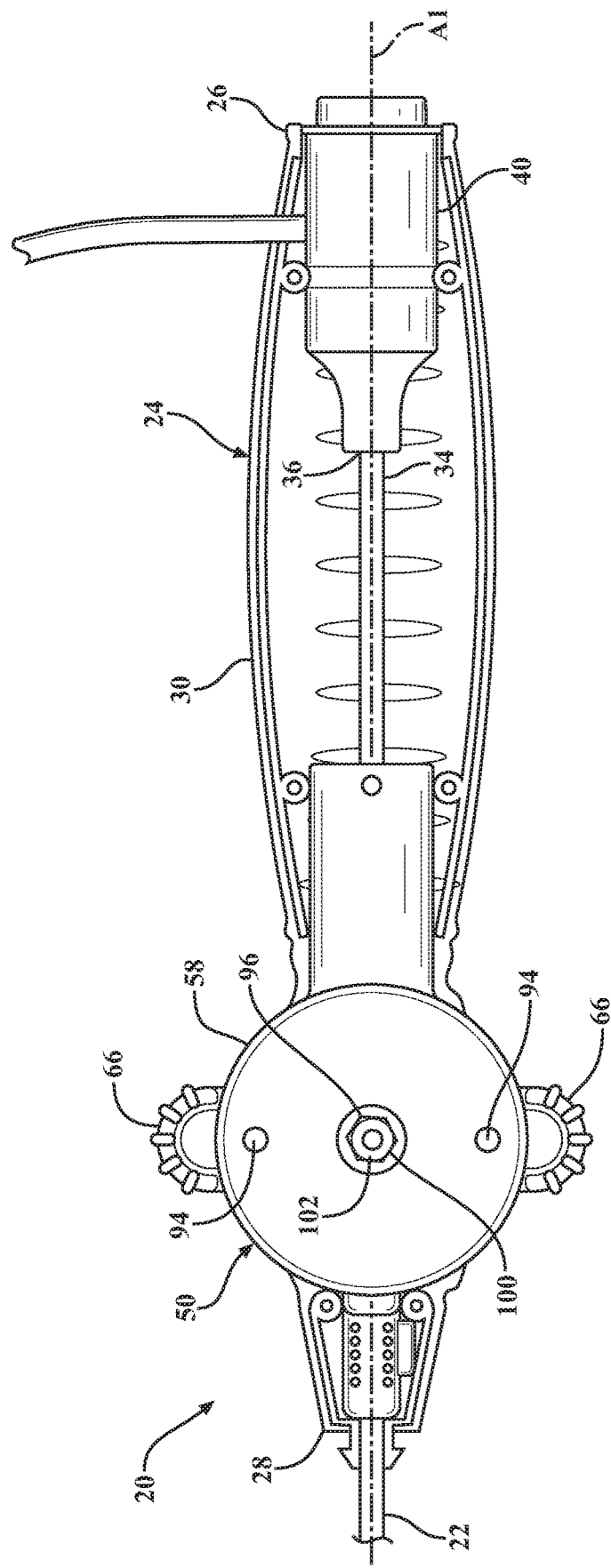
FIG. 4 is a partial cutaway view of the second side of the handle assembly illustrating a valve assembly disposed adjacent to the proximal end of the handle and a lumen extending from a receiving end disposed in sealed communication with the lumen to a distal tip that extends outwardly from the distal end of the handle.
Figure 5:
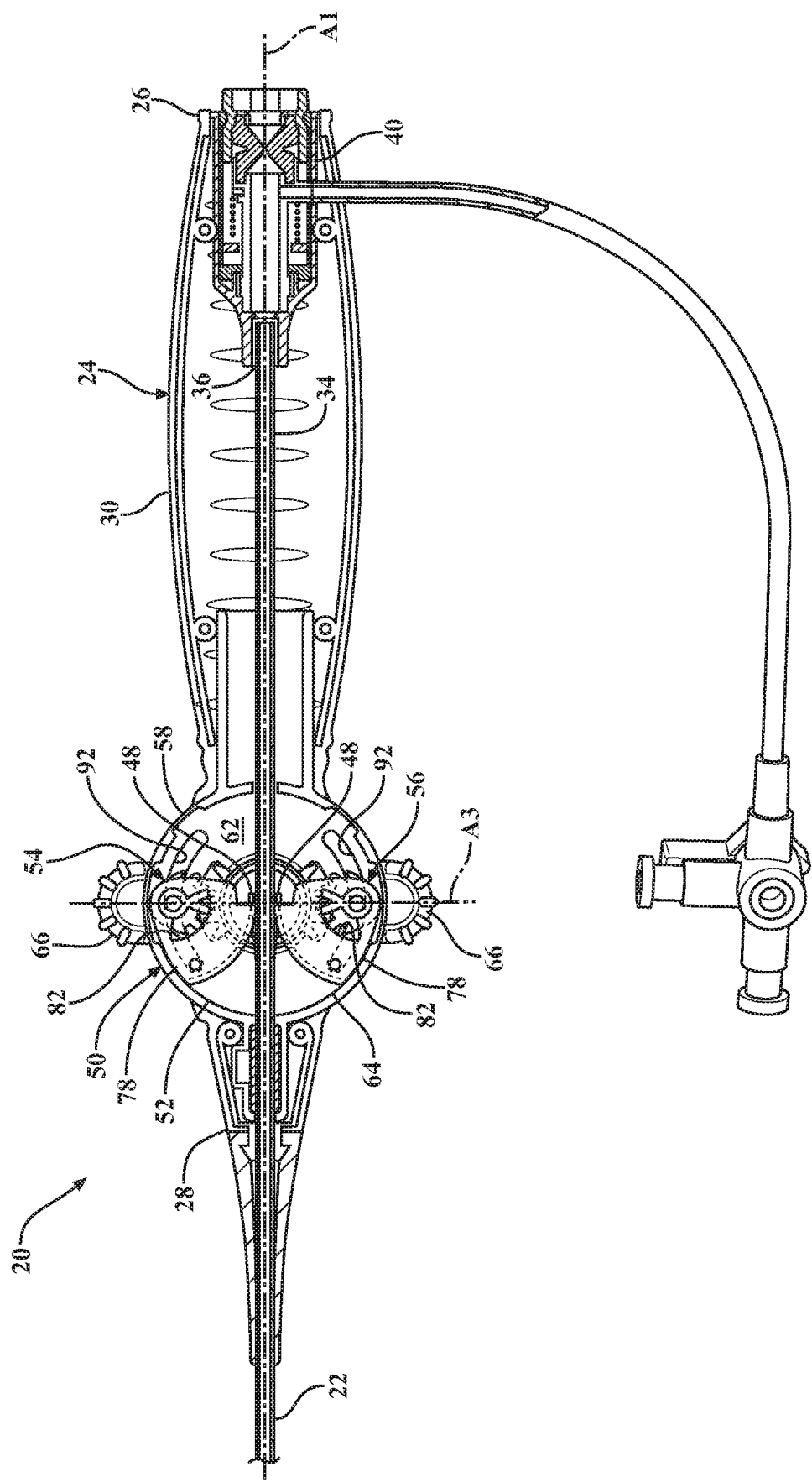
FIG. 5 is a cutaway view of the first side of the handle assembly illustrating the lever disposed in a centered neutral position and the lever assembly including a first and second gear assembly disposed in opposing relationship to one another and offset relative to the longitudinal axis for allowing the lumen to pass therebetween.

Example embodiments will now be described more fully with reference to the accompanying drawings. The example embodiments are provided so that this disclosure will be thorough and fully convey the scope to those skilled in the art. Numerous specific details are set forth such as examples of specific components, devices, mechanisms, assemblies, and methods to provide a thorough understanding of various embodiments of the present disclosure. It will be apparent to those skilled in the art that specific details need not be employed, that example embodiments may be embodied in many different forms, and that neither should be construed to limit the scope of the disclosure. In some examples, well-known processes, well-known device structures, and well-known technologies are not described in detail.

Referring to the drawings, wherein like numerals indicate corresponding parts throughout the several views, a handle assembly 20 for supporting and controlling a steerable catheter 22 is generally shown in FIGS. 1-11. The steerable catheter 22 is the type generally used for directing a medical device, such as a guide wire, catheter, stent, filter, or vessel occlusion device, into a vessel of a patient. As best shown in FIGS. 1-11, the handle assembly 20 includes a handle 24 extending about a longitudinal axis A1 from a proximal end 26 to a distal end 28. In a preferred arrangement, the handle 24 is comprised of a first handle housing 30 and second handle housing 32 which are disposed in fitted engagement with one another for housing a portion of the steerable catheter 22. However, other means of forming the handle 24 can be utilized without departing from the scope of the subject disclosure.

As best shown in FIGS. 3-11, the steerable catheter 22 includes a lumen 34 that extends through the handle 24 along the longitudinal axis A1 from a receiving end 36 disposed adjacent the proximal end 26 of the handle 24 to a distal tip 38 that extends outwardly from and terminates in spaced relationship with the distal end 28 of the handle 24. As best shown in FIGS. 3-5 and 11, a valve assembly 40 is disposed adjacent to the proximal end 26 of the handle 24 and in sealed fluid communication with the receiving end 36 of the lumen 34 for allowing the medical device to be received and passed through the lumen 34 and towards the distal end 28 for use during a medical procedure on a patient. A preferred example of the valve assembly 40 is disclosed in U.S. Pat. No. 9,884,175, the disclosure of which is incorporated herein by reference. However, other valve assemblies may be used without departing from the scope of the subject disclosure.

As best shown in FIGS. 5-10, a pair of control wires 42, 44 are interconnected to the distal tip 38 and extend through the lumen 34 from the distal tip 38 to wire ends 46 disposed inside the handle 24. Each of the control wires 42, 44 have a wire cross-section and include a wire head 48 at the wire ends 46 having a wire head 48 cross-section that is larger than the wire cross-section. As will be explained in more detail below, the wire ends 46 facilitate a pulling action on the control wires 42, 44 to effectuate deflection of the distal tip 38 of the lumen 34.

Figure 6:
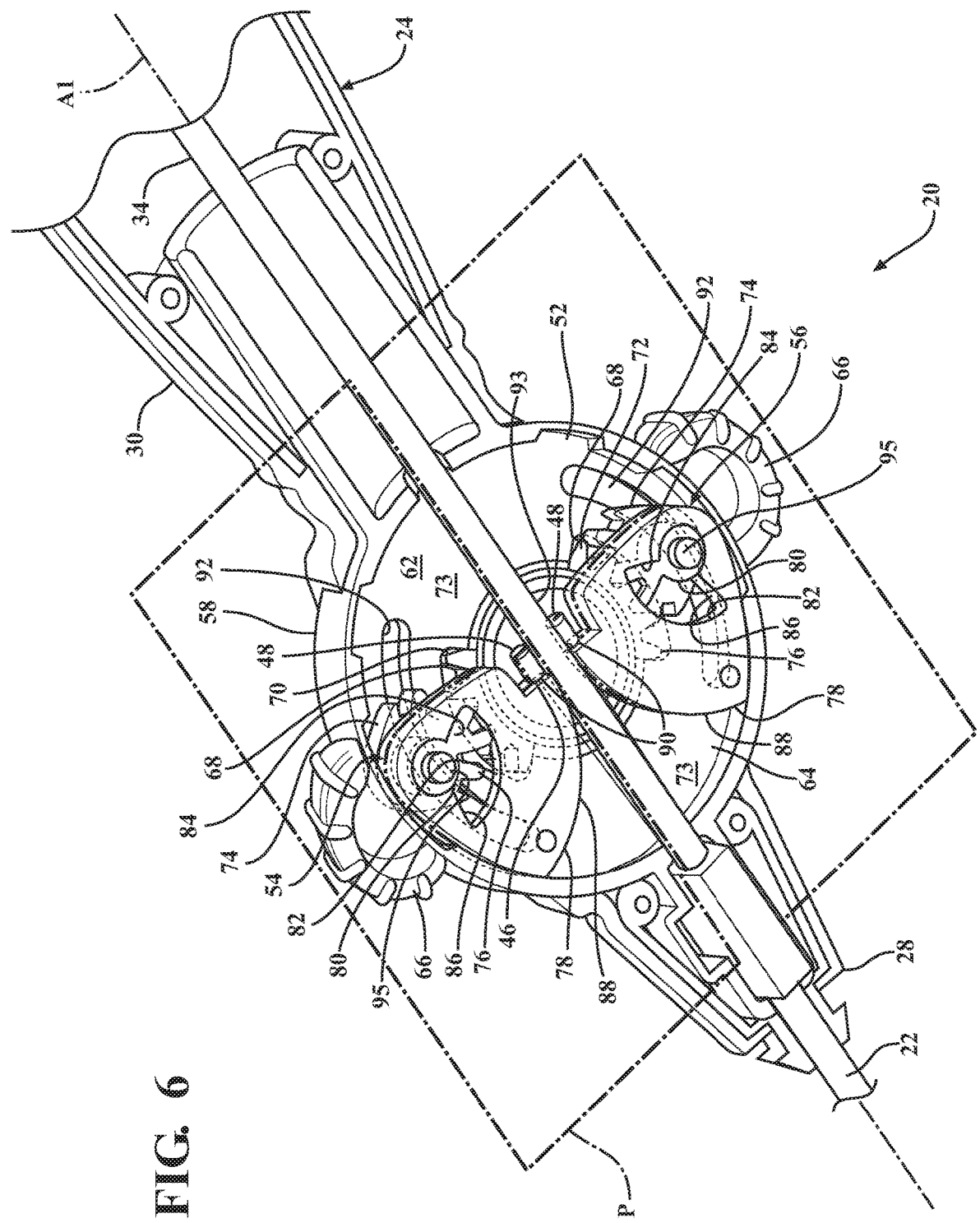
FIG. 6 is a magnified perspective view of a portion of FIG. 5 illustrating a plane extending parallel with and passing through the lumen and the longitudinal axis and illustrating the first and second gear assemblies each including a pulley segment aligned along the plane and radially offset from the longitudinal axis.
Figure 7:
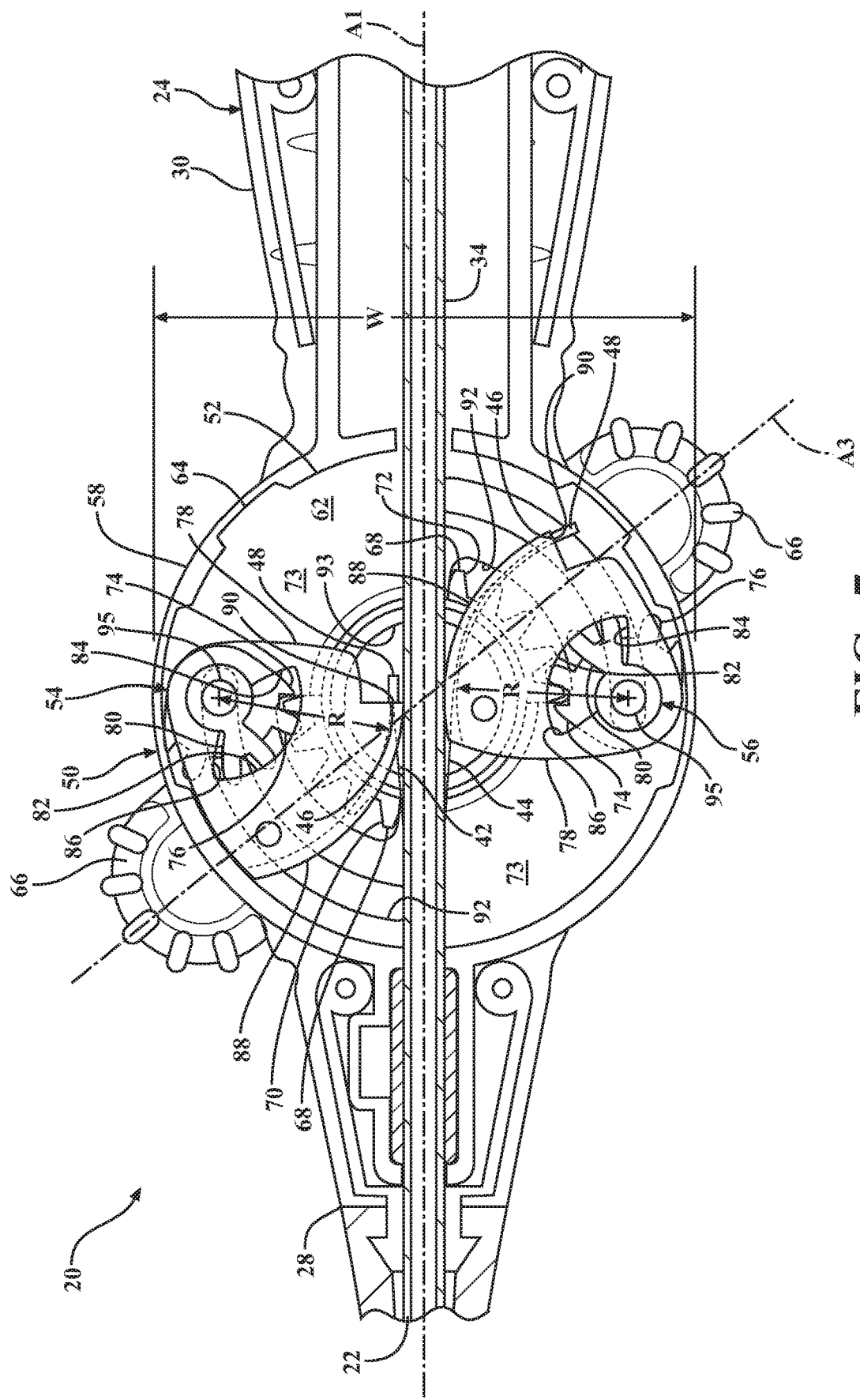
FIG. 7 is a magnified cutaway view of the first side of the handle assembly illustrating the lever rotated from the centered position to a counterclockwise position for rotating one of the pulley segments toward the proximal end of the handle to pull a respective one of the control wires while the other one of the pulley segments rotates towards the distal end of the handle.
Figure 10:
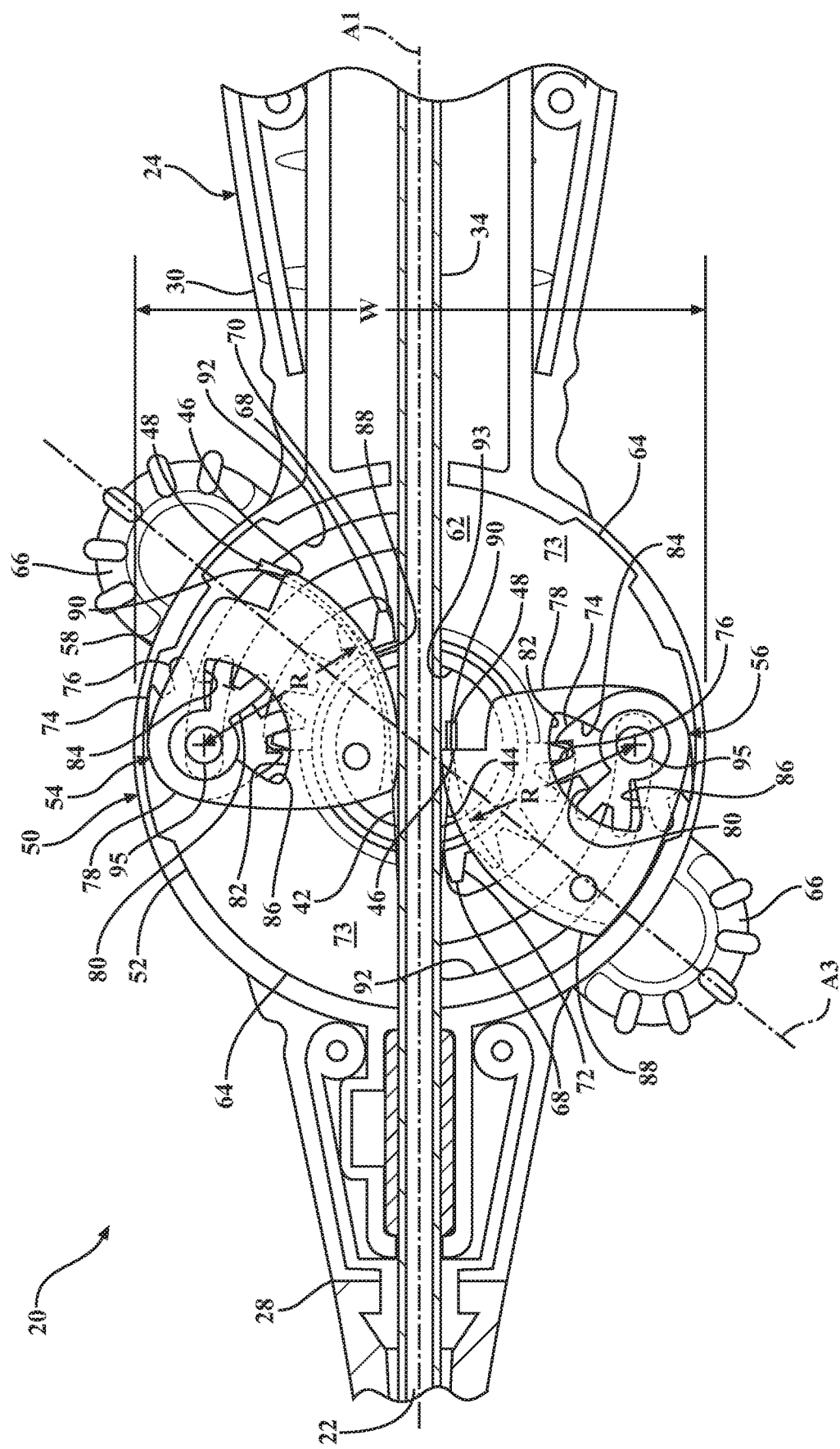
FIG. 10 is a magnified cutaway view of the first side of the handle assembly illustrating the lever rotated clockwise from the centered position to a clockwise position for rotating the other one of the pulley segments toward the proximal end of the handle to pulled a respective other one of the control wires toward the proximal end of the handle.

As best shown in FIGS. 3-11, a lever assembly 50 for controlling the steerable catheter 22 is disposed adjacent to the distal end 28 of the handle 24 and is supported between the first handle housing 30 and the second handle housing 32. The lever assembly 50 includes a lever 52 that is rotatable about a lever axis A2 that extends perpendicular to and intersects the longitudinal axis A1. The lever 52 is rotatable between a counterclockwise position, as shown in FIG. 7, and a clockwise position, as shown in FIG. 10 to cause deflection of the distal tip 38 of the lumen 34 in two opposing directions. When used within this application, the terms "clockwise" and "counterclockwise" are discussed relative to the view shown in FIGS. 1, 3, and 5-10.

As best shown in FIGS. 3 and 5-10, the lever assembly 50 includes a first gear assembly 54 and a second gear assembly 56 disposed in opposing relationship to one another and offset relative to the longitudinal axis A1 to allow the lumen 34 to pass therebetween. Allowing the lumen 34 to pass along the longitudinal axis A1 prevents unnecessary bends in the lumen 34, and thus the medical device inserted into the lumen 34 by way of the valve assembly 40. This eases insertion and removal of the medical device within the lumen 34, reducing the time and difficulty of medical procedures in which the handle assembly 20 is used. Each of the first and second gear assemblies 54, 56 are interconnected to a respective one of the control wires 42, 44 for effectuating individual pulling of the control wires 42, 44 in response to rotation of the lever 52 between the counterclockwise position, shown in FIG. 7, and the clockwise position, shown in FIG. 10. In other words, as will be described in more detail below, when the lever 52 is rotated into the clockwise position, shown in FIG. 6, one of the gear assemblies 54, 56 pulls on one of the control wires 42, 44 while the other one of the gear assemblies 54, 56 does not pull the other one of the control wires 42, 44. Similarly, when the lever 52 is rotated into the clockwise position, as shown in FIG. 10, the pulling action reverses, with the other one of the gear assemblies 54, 56 now pulling the other one of the control wires 42, 44 while the initial one of the gear assemblies 54, 56 does not pull the respective control wire 42, 44. Individually pulling, and not pushing, the control wires 42, 44 prevents the application of compressive force to the control wires 42, 44, preventing buckling and damage to the control wires 42, 44 during deflection of the distal tip 38

As best shown in FIGS. 3-11, the lever assembly 50 includes a first lever housing 58 and a second lever housing 60 disposed in fitted engagement with one another to define a lever volume 62 housing the first and second gear assemblies 54, 56. As best shown in FIGS. 3 and 5-11, the lever 52 includes a rotatable disk 64 disposed between the first lever housing 58 and the second lever housing 60. As best shown in FIG. 6, the rotatable disk 64 is disposed parallel to and offset from a plane P defined as passing through the longitudinal axis A1 and the lumen 34, and being perpendicular to the lever axis A2. The rotatable disk 64 is rotatably aligned on the lever axis A2 and is operably interconnected with the first and second gear assemblies 54, 56.

As best shown in FIGS. 1-10, the lever 52 includes a pair of lever studs 66 that extend radially outward from the rotatable disk 64 in opposing and aligned relationship to one another to define a lever line A3 aligned with the pair of lever studs 66, and preferably intersecting the lever axis A2 at a right angle. The lever 52 has a centered position, best shown in FIGS. 5, 6, and 7, when the lever line A3 is disposed perpendicular to the longitudinal axis A1. In the counterclockwise position, best shown in FIG. 7, the lever line A3 is rotated counterclockwise relative to the centered position, i.e., the level line A3 is rotated towards a distal end 38 of the handle 22. In the clockwise position, best shown in FIG. 10, the lever line LA3 is rotated clockwise relative to the centered position, i.e., the level line A3 is rotated towards a proximal end 26 of the handle 22. The lever 52 is freely rotatable from the centered position, shown in FIGS. 5, 6, and 9, to the counterclockwise position, shown in FIG. 7, and the clockwise position, shown in FIG. 10.

As best shown in FIGS. 3 and 5-10, the rotatable disk 64 includes a plurality of central gear teeth 68 annularly arranged about the lever axis A2 and rotatable simultaneously with the rotatable disk 64 for driving the first and second gear assemblies 54, 56 in response to rotation of the lever 52. The plurality of central gear teeth 68 includes a first set of central gear teeth 70 and a second set of central gear teeth 72 disposed arcuately about the lever axis A2 in opposing and mirrored relationship to one another. The separation of the plurality of central gear teeth 68 into the first set of central gear teeth 70 and the second set of central gear teeth 72 creates a pair of gaps 73 that, along with spacing the plurality of central gear teeth 68 from the plane P, prevents contact between the lumen 34 and the plurality of central gear teeth 68.

As best shown in FIGS. 3 and 5-10, each of the first and second gear assemblies 54, 56 include an outboard gear 74 having outboard gear teeth 76 disposed radially outward from and in meshed engagement with a respective one of the first or second set of central gear teeth 70, 72. Each of the outboard gears 74 are rotatable in response to rotation of the lever 52. When the plurality of central gear teeth 68 rotate with the rotatable disk 64 during rotation of the lever 52, the outboard gears 74, being in meshed engagement with the plurality of central gear teeth 68, rotate in response. The outboard gears 74 rotate about respective gear axes A4 extending in parallel and spaced relationship with the lever axis A2. Each of the gear assemblies 54, 56 have a gear ratio between respective outboard gears 74 and the plurality of central gear teeth 68 that is inclusively between 0.6:1 and 0.7:1 (e.g., 12T:18T, 12T:20T, or 11T:18T) to allow for a compact design.

As best shown in FIGS. 3 and 5-10, each of the first and second gear assemblies 54, 56 also include a pulley segment 78 aligned along the plane P and radially offset from the longitudinal axis A1 to allow the lumen 34 to pass between the pulley segments 78. Each of the pulley segments 78 are operably connected to a respective one of the outboard gears 74 and a respective one of the control wires 42, 44 and are pivotable about respective ones of the gear axes A4 in opposite directions to one another in response to rotation of the lever 52, thus moving each of the pulley segments 78 along an arcuate travel path. As the lever 52 rotates from the centered position one of the pulley segments 78 rotates toward the proximal end 26 of the handle 24, and the other pulley segment 78 rotates toward the distal end 28 of the handle 24. As a respective one of the pulley segments 78 moves toward the proximal end 26 of the handle 24, it effectuates the individual pulling of a respective one of the control wires 42, 44 along an arcuate wire path in contact with the respective one of the pulley segments 78. The arcuate wire paths define a bending radius R, that is large relative to one quarter of a width W of the handle 24, allowing for the control wires 42, 44 to be manufactured from materials having a similarly larger bending yield radius that is less than or equal to the bending radius R, allowing for the use of different materials which decrease the cost of the handle assembly 20. In addition, pulling of the control wires 42, 44 along the actuate wire path reduces stress on the control wires 42, 44 and prevents breaking of the control wires 42, 44, resulting in an extending life of the handle assembly 20.

Figure 8:
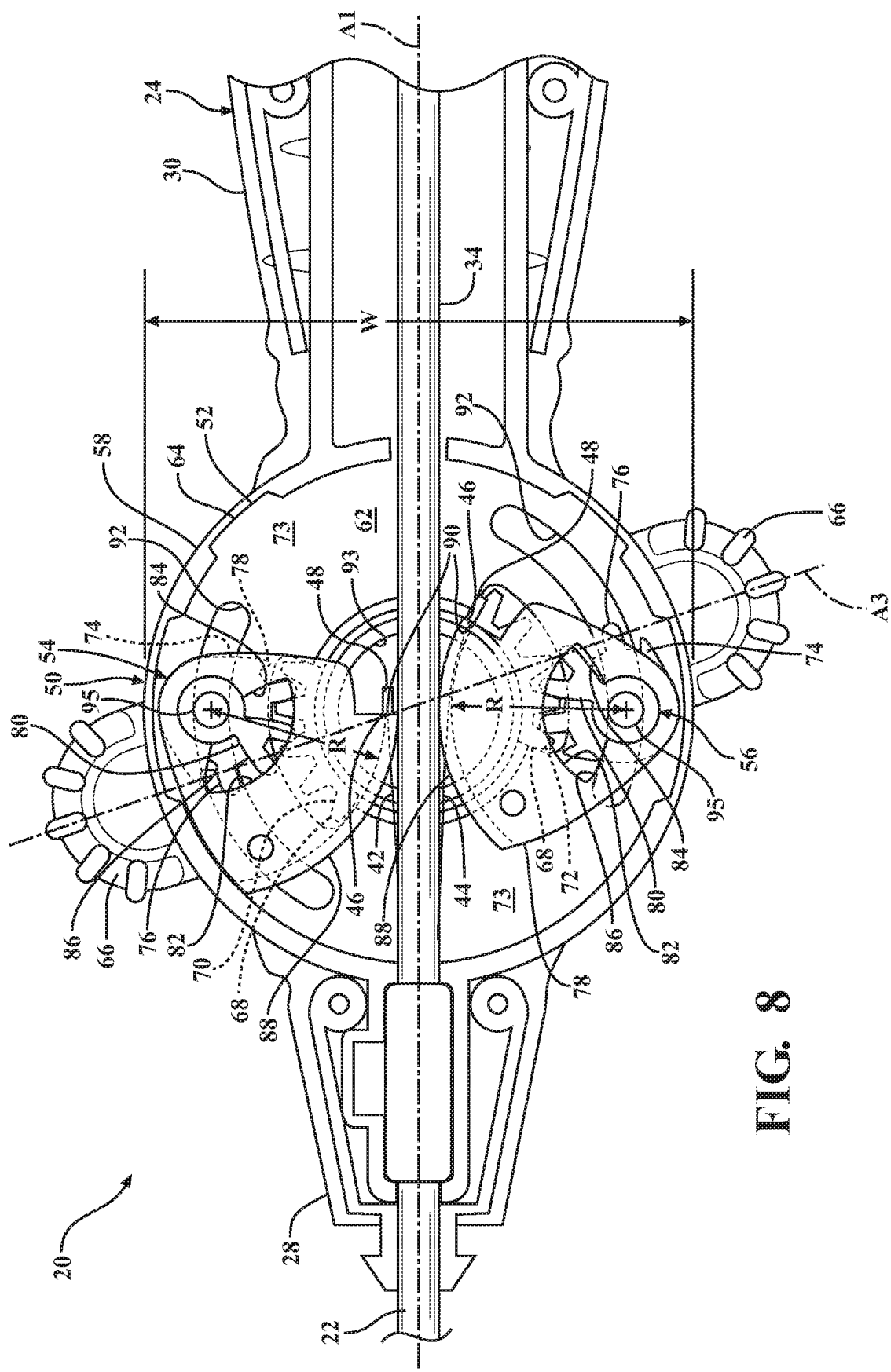
FIG. 8 is a magnified cutaway view of the first side of the handle assembly illustrating the lever partially rotated in a clockwise direction back from the counterclockwise position towards the centered position for releasing the pulling force applied by the rotated pulley segment on the respective one of the control wires and allowing a tension of the respective one of the control wires to rotate the respective one of the pulley segments back toward the distal end of the handle.
Figure 9:
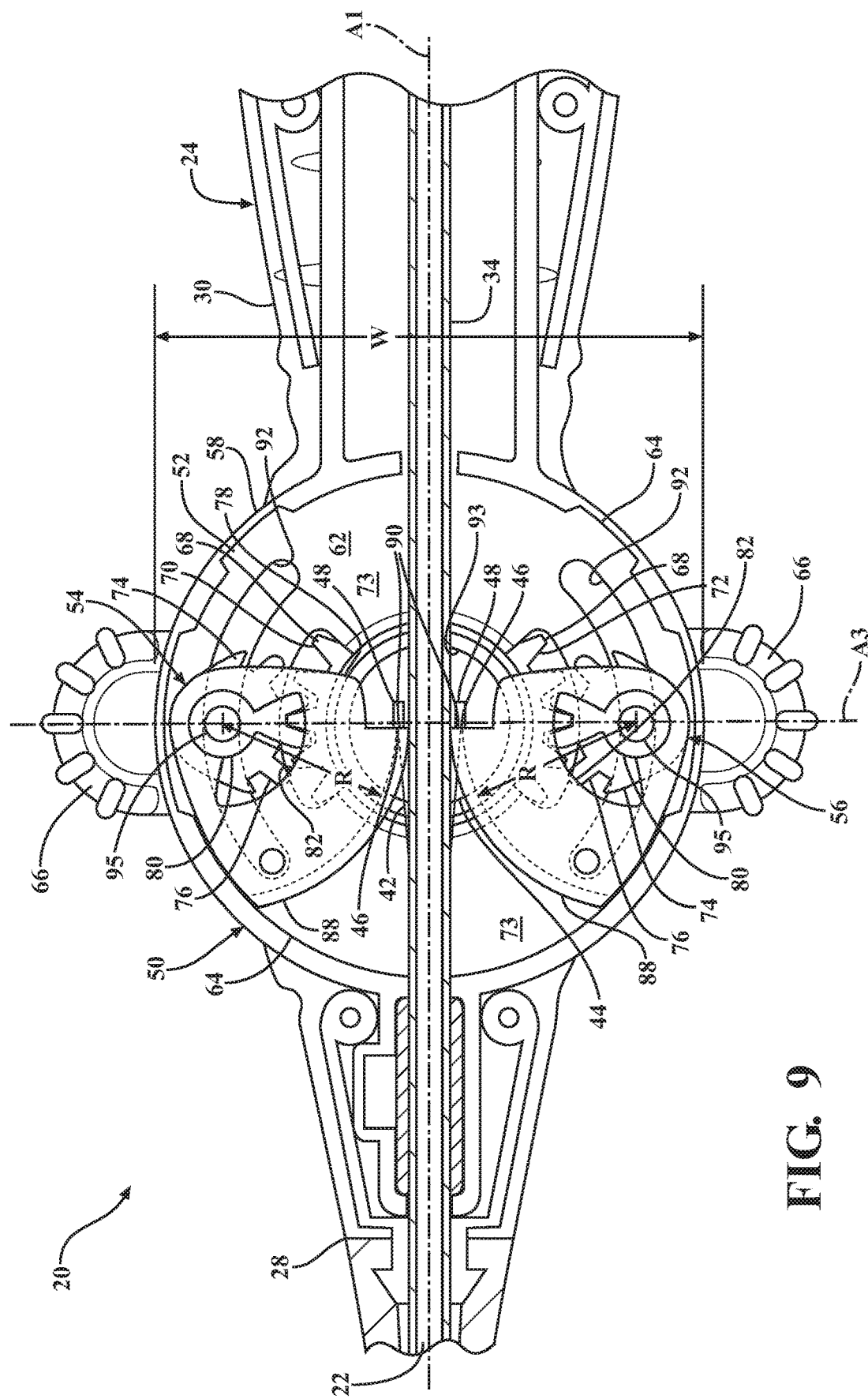
FIG. 9 is magnified cutaway view of the first side of the handle assembly illustrating the lever returned to the centered position and the respective one of the control wires fully rotating the respective one of the pulley segments back into a neutral condition.

As best shown in FIGS. 3 and 5-10, each of the gear assemblies 54, 56 includes a link 80 in fixed and integral engagement with the outboard gear 74 and that contacts the pulley segment 78. The link 80 is pivotable about the gear axis A4 in conjunction with the outboard gear 74 and aligned on the plane P with the pulley segment 78 for driving rotation of the pulley segment 78 about the gear axis A4 in response to rotation of the lever 52. Each of the pulley segments 78 includes a pulley slot 82 that is larger than the link 80 and which extends between a slot back 84 and a slot front 86. Responsive to rotation of the lever 52, the links 80 rotate in opposite directions to one another (e.g., one link 80 rotates toward the proximal end 26 of the handle 24, while another link 80 rotates toward the distal end 28 of the handle 24). Each of the links 80 are disposed in the pulley slot 82 and are pivotable within the pulley slot 82 to engage the slot back 84 during movement of the lever 52 in a first rotational direction (e.g., toward the clockwise position or the counterclockwise position), rotating the pulley segment 78 about the gear axis A4 towards the proximal end 26 to individually pull a respective one of the control wires 42, 44. As best illustrated in FIGS. 3 and 5-10, the pulley segment 78 then freely pivots within the pulley slot 82 from the slot back 84 toward the slot front 86 during movement of the lever 52 in a second rotational direction opposite to the first rotational direction to establish a pulley lost motion connection between the link 80 and the pulley segment 78. This prevents the pulley segment 78 from applying a pushing force to the control wire 42, 44 during the second rotation, and instead the control wire 42, 44 returns as tension is released as the link 80 and, as best shown in FIG. 8, the pulley segment 78 move towards the distal end 28 of the handle 24. In other words, tension on the control wire 42, 44 secured to the pulley segment 78 pulls the pulley segment 78 back towards the centered position as the change in deflection of the distal tip 38 caused by tension on the other control wire 42, 44 secured to the other pulley segment 78 creates a longer path through the lumen 34 for the control wire 42, 44.

As best shown in FIGS. 3 and 5-10, each of the pulley segments 78 is generally pie-shaped and includes a pulley edge 88 for engaging with a respective one of the wire heads 48. The pulley edge 88 pulls the respective one of the wire heads 48 along the arcuate wire path in response to rotation of the lever 52 towards a respective one of the clockwise position or the counterclockwise position (i.e., in a first rotational direction or a second rotational direction), causing the pulley segment 78 to rotate towards the proximal end 26 of the handle 24, as best shown in FIGS. 7 and 10. The pulley edge 88 provides a wide surface against which the control wire 42, 44 is wrapped, resulting in a large bending radius and less bending strain being applied to the control wire 42, 44.

As best shown in FIGS. 6-9 and 11, each of the pulley segments 78 defines a wire opening 90 proximate to the pulley edge 88 and a respective one of the control wires 42, 44 is slideably disposed in the wire opening 90 for allowing the control wires 42, 44 to slide freely during rotation of the pulley segment 78 towards the distal end 28 of the handle 24. This arrangement establishes a wire lost motion connection allowing for pull-only engagement of the control wires 42, 44 without requiring the use of elastic material in the control wires 42, 44. Elastic, when used herein, means that the control wires 42, 44 are made of a material that stretches substantially in the axial direction. The wire opening 90 may be closed (i.e., a hole) or open (i.e., a slot). The wire opening 90 is sized and shaped such that the wire head 48 cannot fit through the wire opening 90 but the control wire 42, 44 can move freely through the wire opening 90. This prevents the pulley segment 78 from applying a pushing force to the control wire 42, 44 during the second rotation, and instead the control wire 42, 44 returns based on tension caused by pulling of the control wire 42, 44 resulting from having a longer path (i.e., an outer path) as the other control wire 42, 44 is pulled by the other pulley segment 78. By using both the wire lost motion connection and the pulley lost motion connection, the pulley segment 78 is returned as the wire head 48 applies a force to the pulley segment 78 to pull the pulley segment 78 back toward the distal end 28 during the second rotation, meaning that the control wires 42, 44 are only under tension and not compression. The combination of the wire lost motion connection and the pulley lost motion connection allow for a compact design of the lever assembly 50 while allowing for a substantial lost motion range.

As best shown in FIGS. 3 and 5-10, the rotatable disk 64 defines a pair of arcuate disk slots 92 that extend arcuately about the lever axis A2 in opposing and mirrored relationship to one another and a central disk hole 93 aligned on the longitudinal axis A1. The lever assembly 50 further includes a pair of support pins 95 that extend along a respective one of the gear axes A4 and rotatably support the outboard gear 74, the link 80, and the pulley segment 78. Each of the support pins 95 pass through and engage respective ones of the pair of arcuate disk slots 92 to allow for rotation of the rotatable disk 64 as the arcuate disk slots 92 travel about the support pins 95. Put another way, the support pins 95 stay still as the rotatable disk 64 rotates, with the arcuate disk slots 92 provide a path allowing for the rotation.

As best shown in FIGS. 3 and 4, the first lever housing 58 defines a first pair of outer pin holes 94 disposed in opposing relationship to one another and each aligned on respective ones of the gear axes A4. The second lever housing 60 defines a second pair of outer pin holes 97 disposed in opposing relationship to one another and each aligned on respective ones of the gear axes A4, and the support pins 95 extending between the first pair of outer pin holes 94 to the second pair of outer pin holes 94.

In operation, rotation of the rotatable disk 64 initiated by a user applying force to at least one of the lever studs 66, results in rotation of the rotatable disk 64 and travel of the support pins 95 through the arcuate disk slots 92. The plurality of central gear teeth 68 rotate with the rotatable disk 64, causing rotation of the outboard gears 74 and the links 80. One of the links 80 engages one of the slot backs 84, causing rotation of a respective one of the pulley segments 78, which pulls a respective one of the control wires 42, 44, which causes deflection of the distal tip 38 of the lumen 34.

Figure 11:
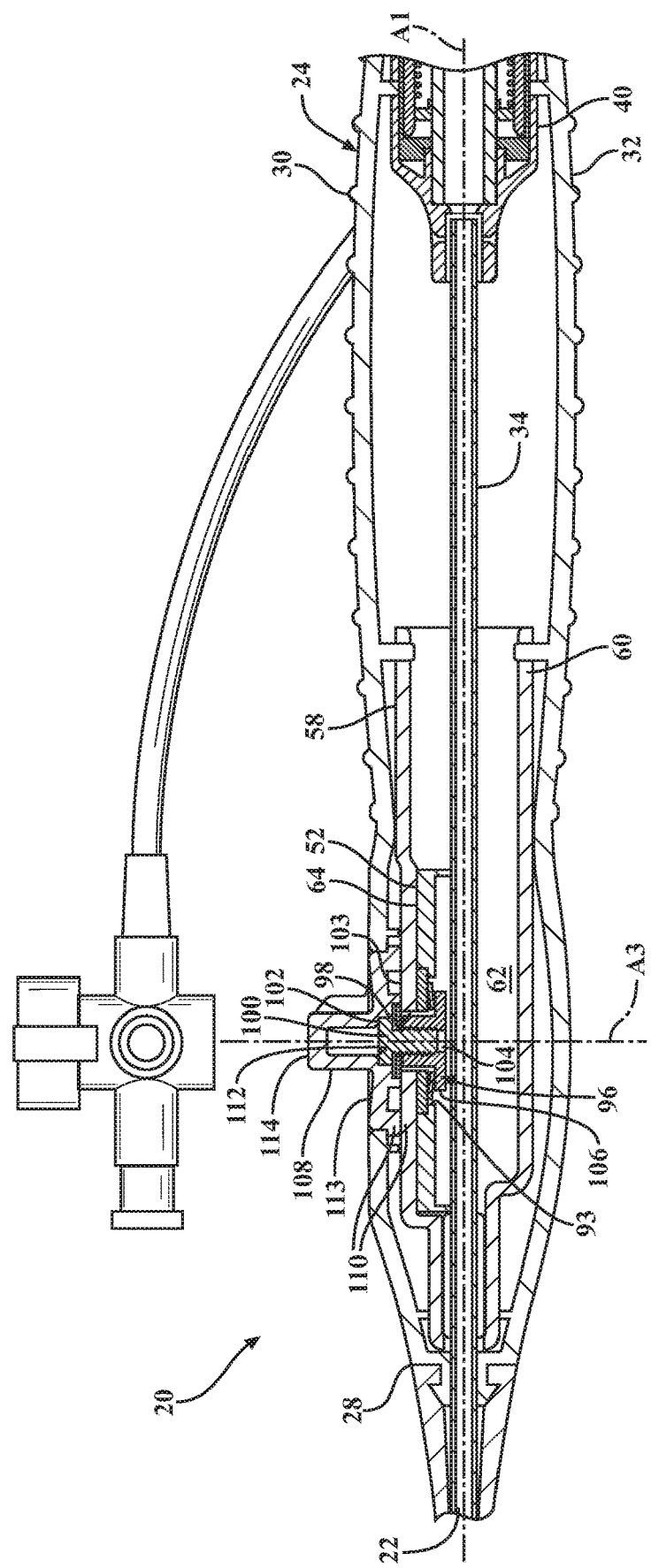
FIG. 11 is a top cutaway view of the handle assembly illustrating the arrangement of components in the handle assembly, in particular a rotatable disk of the lever being offset from the lumen.

As best shown in FIGS. 3, 4, and 11, the lever assembly 50 further includes a tensioning mechanism 96 for allowing a user to increase a resistance to rotation of the lever 52. The tensioning mechanism 96 allows for different users of the handle assembly 20 to apply different resistances of rotation of the lever 52 Further, this allows for the user to increase the resistance to rotation of the lever 52 to be so high as to prevent accidental rotation of the lever 52, thus allowing the user to prevent accidental change in deflection of the distal tip 38 of the lumen 34. To enable the tensioning mechanism 96, the first lever housing 58 defines a central housing hole 98 disposed between the first pair of outer pin holes 94. The tensioning mechanism 96 includes a central bolt 100 that has a head 102 disposed along an outer surface 103 of the first lever housing 58 and a shank 104 that extends through the central housing hole 98, the central disk hole 93, and along the lever axis A2. The tensioning mechanism 96 further includes a central nut 106 disposed between the first lever housing 58 and the second lever housing 60, about the lever axis A2, in fixed engagement with the rotatable disk 64, and in threaded engagement with the central bolt 100.

The tensioning mechanism 96 further includes a fastener tightener 108 having a generally disk shape. The fastener tightener 108 includes a first tightener side 110 that defines a recess 112 corresponding to the head 102 of the central bolt 100. The fastener tightener 108 includes a second tightener side 113 that is opposite the first tightener side 110 and has a raised action member 114 extending from the second tightener side 113 for allowing the user to tighten or loosen the central bolt 100 by applying a rotational force to the raised action member 114. This tightening or loosening results in an increase or decrease of the rotational force required to be applied to the lever studs 66 to rotate the rotatable disk 64 relative to the first lever housing 58 and the second lever housing 60. As best shown in FIGS. 2 and 3, the first handle housing 30 defines a tightener hole 116 for receiving the fastener tightener 108, which allows the raised action member 114 to extend outside of the first handle housing 30, providing access for the user.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A handle assembly for supporting and controlling a steerable catheter, said handle assembly comprising:
   a handle extending about a longitudinal axis from a proximal end to a distal end;
   a lumen extending through said handle along the longitudinal axis from a receiving end disposed adjacent said proximal end to a distal tip extending outwardly from and terminating in spaced relationship with said distal end of said handle;
   a pair of control wires interconnected to said distal tip and extending through said lumen and into said handle;

a lever assembly disposed at least partially within said handle and including a lever rotatable about a lever axis to control deflection of said distal tip of said lumen;

said lever assembly including a first gear assembly and a second gear assembly disposed in opposing relationship to one another and offset relative to the longitudinal axis;

said lumen passing between said first and second gear assemblies; and each of said first and second gear assemblies interconnected to a respective one of said pair of control wires for individually pulling said control wires in response to rotation of said lever.

2. The handle assembly of claim 1, further comprising:

each of said first and second gear assemblies including a pulley segment disposed along a plane extending parallel with and through the longitudinal axis and said lumen; and each of said pulley segments interconnected to one of said control wires and pivotable in opposite directions relative to one another in response to rotation of said lever in a first rotational direction and a second rotational direction opposite the first rotational direction for alternatively pulling said respective one of said control wires along an arcuate wire path.

3. The handle assembly of claim 2, wherein each of said first and second gear assemblies include an outboard gear radially offset from and operably connected to a respective one of said pulley segments; and each of said outboard gears being rotatable about respective gear axes in opposite directions relative to one another in response to rotation of said lever.

4. The handle assembly of claim 3, further comprising:

each of said gear assemblies including a link extending between said outboard gear and said pulley segment and pivotable in conjunction with said outboard gear for driving rotation of said pulley segment about the gear axis in response to rotation of said lever.

5. The handle assembly of claim 4, wherein said link is disposed within said plane in fixed and integral engagement with said outboard gear.

6. The handle assembly of claim 5, further comprising:

each of said pulley segments defining a pulley slot being larger than said link and extending between a slot back and a slot front;

each of said links being pivotably disposed in a respective one of said pulley slots for pivoting within said respective one of said pulley slots to engage said slot back during movement of said lever in one of the first or second rotational directions for rotating said respective one of said pulley segments towards said proximal end to individually pull a respective one of said control wires and to freely pivot within said pulley slot from said slot back towards said slot front during movement of said lever in the other of said first or second rotational directions to establish a first pulley lost motion connection between said respective one of said links and said respective one of said pulley segments.

7. The handle assembly of claim 6, further comprising:

said control wires each including a wire head disposed at a wire end of each of said control wires within said handle;

each of said pulley segments being generally pie-shaped to define a pulley edge for engaging with a respective one of said wire heads and pulling said respective one of said wire heads along said arcuate wire path in response to rotation of said lever in a respective one of the first rotational direction or the second rotational direction.

8. The handle assembly of claim 7, further comprising:

each of said pulley segments defining a wire opening proximate to the pulley edge for engaging with a respective one of said wire heads; and a respective one of said control wires slideably disposed in said wire opening for allowing said control wires to slide freely within said wire opening during rotation of said pulley segment towards said distal end of said handle to establish a wire lost motion connection allowing for pull-only engagement of said control wires.

9. The handle assembly of claim 4, further comprising:

said lever including a rotatable disk disposed parallel to and offset from the plane in rotatably aligned relationship with the lever axis and operably interconnected with said outboard gears of said first and second gear assemblies for driving rotation of said pulley segments in response to rotation of said rotatable disk.

10. The handle assembly of claim 9, further comprising:

said rotatable disk including a plurality of central gear teeth annularly arranged about the lever axis and rotatable simultaneously with said rotatable disk;

each of said outboard gears having outboard gear teeth disposed radially outward from and in meshed engagement with said plurality of central gear teeth for driving said outboard gears in response to rotation of said rotatable disk by said lever.

11. The handle assembly of claim 10, further comprising:

said plurality of central gear teeth including a first set of central gear teeth and a second set of central gear teeth disposed arcuately about said lever axis in opposing and mirrored relationship to one another.

12. The handle assembly of claim 10, wherein each of said gear assemblies has a gear ratio between respective outboard gears and said plurality of central gear teeth of between 0.6:1 and 0.7:1.

13. The handle assembly of claim 10, further comprising:

said rotatable disk defining a pair of arcuate disk slots extending arcuately about said lever axis in opposing and mirrored relationship to one another;

said lever assembly including a pair of support pins each extending along a respective one of the gear axes and rotatably supporting respective ones of said outboard gears and said pulley segments; and each of said support pins passing through and engaging respective ones of said pair of arcuate disk slots for allowing rotation of said rotatable disk as said arcuate disk slots travel about said support pins.

14. The handle assembly of claim 9, further comprising:

said lever assembly including a first lever housing and a second lever housing disposed in fitted engagement with one another to define a lever volume housing said first and second gear assemblies.

15. The handle assembly of claim 14, further comprising:

said first lever housing defining a central housing hole;

said rotatable disk defining a central disk hole disposed at a central portion of said rotatable disk;

said lever assembly including a central bolt having a head disposed along an outer surface of said first lever housing and a shank extending through said central housing hole and said central disk hole and along said lever axis;

said lever assembly including a central nut disposed between said first lever housing and said second lever housing and about said lever axis and engaged with said central bolt.

16. The handle assembly of claim 15, further comprising: said lever assembly including a fastener tightener having a generally disk shape and a first tightener side defining a recess corresponding to said head of said central bolt and a second tightener side opposite said first tightener side and having a raised action member extending from said second tightener side for allowing a user to tighten or loosen said central bolt by applying a rotational force to said raised action member and thus increase or decrease the rotational force required to be applied to said lever to rotate said rotatable disk relative to said first lever housing and said second lever housing.

17. The handle assembly of claim 1, further comprising a valve assembly disposed adjacent said proximal end of said handle and in sealed fluid communication with said receiving end opposite said distal tip of said lumen for allowing a medical device to be received at said receiving end and passed through said lumen and towards said distal end for use during a medical procedure on a patient.

\* \* \* \* \*